United States Patent [19]

Dixon et al.

[11] Patent Number: 4,885,313

[45] Date of Patent: Dec. 5, 1989

[54] 3,4-DIHYDROXYPHENYLETHYLAMINE DERIVATIVES AND THEIR USE

[75] Inventors: John Dixon, Melton Mowbray; Francis Ince, Loughborough, both of United Kingdom

[73] Assignee: Fisons plc, Loughborough, England

[21] Appl. No.: 127,365

[22] Filed: Dec. 2, 1987

Related U.S. Application Data

[62] Division of Ser. No. 662,393, Oct. 18, 1984, Pat. No. 4,720,586.

[30] Foreign Application Priority Data

| Dec. 6, 1983 [GB] | United Kingdom | 8332447 |
| Dec. 6, 1983 [GB] | United Kingdom | 8332448 |
| Dec. 6, 1983 [GB] | United Kingdom | 8332452 |
| Jan. 24, 1984 [GB] | United Kingdom | 8401746 |
| Jan. 24, 1984 [GB] | United Kingdom | 8401747 |
| Jan. 24, 1984 [GB] | United Kingdom | 8401748 |
| Jan. 24, 1984 [GB] | United Kingdom | 8401750 |

[51] Int. Cl.$^4$ .......................................... C07C 103/22
[52] U.S. Cl. .................................... 514/620; 514/821; 564/185; 564/186; 564/187
[58] Field of Search ................. 564/185, 186, 187; 558/415; 514/620, 613, 821

[56] References Cited

U.S. PATENT DOCUMENTS

| 2,233,296 | 2/1941 | Nelles et al. | 564/185 |
| 4,311,706 | 1/1982 | Bodor et al. | 654/185 |
| 4,381,305 | 4/1983 | Casagrande et al. | 564/185 |
| 4,562,201 | 12/1985 | Stout et al. | 564/185 |

*Primary Examiner*—Richard L. Raymond
*Assistant Examiner*—Raymond Covington
*Attorney, Agent, or Firm*—Marshall, O'Toole, Gerstein, Murray & Bicknell

[57] ABSTRACT

Novel 3,4-dihydroxyphenylethylamine derivatives possess dopaminergic activity in animals and are therefore useful in the treatment of inter alia congestive heart failure, renal failure and reversible obstructive airways disease.

The compounds are generally administered in the form of a pharmaceutical composition comprising the active ingredient in admixture with a pharmaceutically acceptable adjuvant, diluent or carrier.

9 Claims, No Drawings

3,4-DIHYDROXYPHENYLETHYLAMINE DERIVATIVES AND THEIR USE

This is a division of application Ser. No. 662,393 filed Oct. 18, 1984 now U.S. Pat. No. 4,720,586.

This invention relates to new compounds, processes for their preparation and compositions containing them.

According to the invention we provide the compounds of formula I,

I

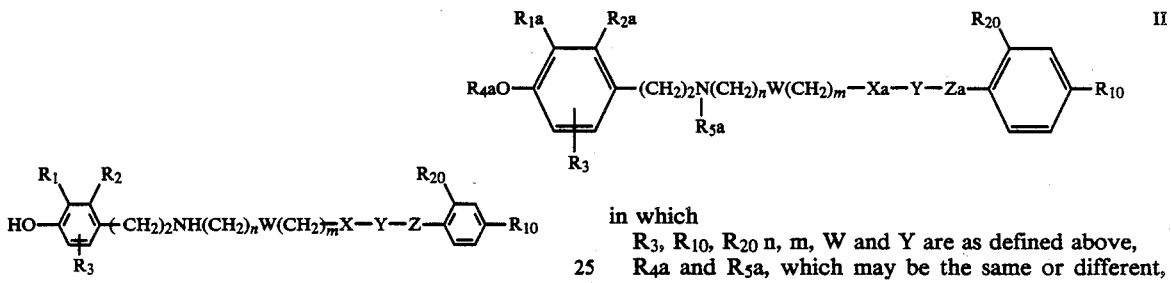

in which $R_1$ represents OH, $R_2$ and $R_3$, which may be the same or different, each independently represent hydrogen, fluorine, chlorine, bromine, alkyl $C_1$ to $C_6$, nitro, nitrile, $(CH_2)_p R_9$ or $SR_9$, W represents a single bond, a 1,2; 1,3; or 1,4-phenylene ring; a —CH=CH— group or a 1,4-cyclohexanediyl group;

X represents NH, O, S, $SO_2$, CO, $CH_2$, CONH or —COO;

Y represents $(CH_2)_q$, CO, CS, $SO_2$ and $R_{20}$ represents hydrogen, or Y represents $CR_{15}R_{16}CR_{17}R_{18}$, wherein the carbon atom bearing $R_{15}$ and $R_{16}$ is adjacent to X and in which $R_{17}$ and $R_{18}$, together with the carbon atom to which they are attached form a carbonyl group, and $R_{15}$, $R_{16}$ and $R_{20}$ each represent hydrogen, or $R_{15}$ and $R_{20}$ together form a chain —$CH_2$—, and $R_{16}$, $R_{17}$ and $R_{18}$ each represent hydrogen, or $R_{15}$, $R_{16}$, $R_{17}$ and $R_{18}$ each independently represent hydrogen or alkyl C1 to 6 and $R_{20}$ represents hydrogen;

Z represents a single bond, $NR_{19}$, $CH_2$, O, CO, S or $SO_2$,
in which $R_{19}$ represents hydrogen or alkyl C1 to 6;

n, and m each independently represent an integer from 1 to 4 inclusive;

q represents an integer from 1 to 3 inclusive;

p represents 0 or an integer from 1 to 3 inclusive;

$R_9$ represents phenyl or phenyl substituted by hydroxy, and $R_{10}$ represents hydrogen or chlorine, provided that (i) when $R_1$ represents —OH, $R_2$ and $R_3$ both represent hydrogen, X represents NH, Y represents $(CH_2)_q$, Z represents a single bond and $R_{20}$ represents hydrogen, W does not represent a single bond;

(ii) when $R_1$ represents —OH, $R_2$ and $R_3$ both represent hydrogen, W represents a single bond, X represents NH and Z represents a single bond, then at least one of $R_{15}$, $R_{16}$, $R_{17}$ and $R_{18}$ is alkyl C1 to 6;

(iii) when X represents $SO_2$, CO, COO or CONH, then Y does not represent CO, CS or $SO_2$;

(iv) when Y represents CO, CS or $SO_2$, then Z does not represent CO or $SO_2$, and pharmaceutically acceptable derivatives thereof The invention also provides the compounds of formula I and their pharmaceutically acceptable derivatives, as pharmaceuticals.

According to our invention we also provide a process for the production of a compound of formula I, or a pharmaceutically acceptable derivative thereof, which comprises removal of at least one protecting group from a compound of formula II,

II $$R_{4a}O-\underset{R_3}{\underset{|}{\bigcirc}}\overset{R_{1a}}{\underset{}{}}\overset{R_{2a}}{\underset{}{}}-(CH_2)_2N(CH_2)_nW(CH_2)_m-X_a-Y-Z_a-\underset{}{\bigcirc}\overset{R_{20}}{\underset{}{}}-R_{10}$$
$$\underset{R_{5a}}{|}$$

in which $R_3$, $R_{10}$, $R_{20}$ n, m, W and Y are as defined above, $R_{4a}$ and $R_{5a}$, which may be the same or different, each represent hydrogen or a protecting group, $R_{1a}$, $R_{2a}$, $X_a$ and $Z_a$ have the same respective meanings as $R_1$, $R_2$, X and Z defined above, save that in addition $R_{1a}$ represents $OR_{6a}$, $X_a$ may represent $NR_{8a}$, in which $R_{8a}$ represents a protecting group, $Z_a$ may represent $NR_{19a}$, in which $R_{19a}$ has the same meaning as $R_{19}$ defined above, save that in addition, $R_{19a}$ may represent a protecting group, provided that the compound of formula II bears at least one protecting group, and where desired or necessary converting the resulting compound of formula I to a pharmaceutically acceptable derivative thereof, or vice versa.

Protecting groups that $R_{4a}$, $R_{5a}$, $R_{6a}$, $R_{8a}$, and $R_{19a}$ may represent include, for example, alkyl C1 to 6, especially methyl; phenylalkyl C7 to 12, especially benzyl; alkanoyl C2 to 6, such as acetyl, and haloalkanoyl C2 to 6, especially trifluoroacetyl. In addition, the protecting group may protect two functional groups, for example $R_{4a}$ and $R_{7a}$ may together represent $(CH_3)_2C<$. Other protecting groups are well known and include those described in Protective Groups in Organic Chemistry, ed: J W F McOmie, Plenum Press (1973), and Protective Groups in Organic Synthesis, T. W. Greene, Wiley-Interscience (1981).

Removal of the protecting group depends on the nature of the protecting group; conventional techniques may generally be employed, including acidic or basic cleavage or hydrogenolysis. For example, protecting alkyl or phenylalkyl groups may be removed by cleavage using a protic acid, e.g. hydrochloric acid or hydrobromic acid at a temperature of from 0° to 150° C. or a Lewis acid, e.g. by reacting with boron trihalide in a halocarbon solvent When the protecting group is alkanoyl or haloalkanoyl, cleavage may be effected using a base, e.g. sodium hydroxide, in a suitable solvent, e.g. aqueous ethanol Lewis bases, e.g. pyridine hydrochloride, may be used to cleave alkyl or phenylalkyl groups. 1-Phenylalkyl groups, e.g. benzyl, may be removed by catalytic hydrogenation using a suitable catalyst, e.g. palladium, in a suitable solvent, e.g. ethanol, or acetic acid. Further methods for the removal of protecting groups are described in both McOmie and Greene, loc. cit. Both McOmie and Greene also described numerous methods for the application of protecting groups.

When none of Xa, Y or Za represents CO, CS, COO, CONH or SO$_2$, compounds of formula II may be made by reducing a compound of formula III,

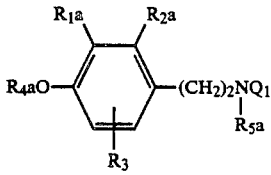
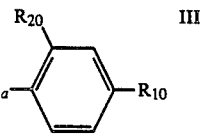

in which one or both of $Q_1$ and $Q_2$ represents CO, and the other represents $CH_2$, and $R_{1a}$, $R_{2a}$, $R_3$, $R_{4a}$, $R_{5a}$, $R_{10}$, $R_{20}$, W, Xa, Y, Za, n and m are as defined above.

The reducing agent may be electrophilic, for example diborane, or nucleophilic, for example, a complex metal hydride such as lithium aluminium hydride or sodium (2-methoxyethoxy)aluminium hydride. The reaction may be carried out in a suitable solvent inert to the reaction conditions. Aprotic solvents are preferred, for example tetrahydrofuran, diethyl ether or 1,2-dimethoxyethane. The reaction may be carried out at a temperature of, for example, from 0° to 100° C.

When Xa represents N the compounds of formula III may be made by sequentially reacting the groups $L_1$, and $L_2$, in any order of the corresponding compound of formula IV,

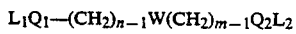

in which one of $L_1$ and $L_2$ represents a good leaving group and the other of $L_1$ and $L_2$ represents either a good leaving group or a group which may be readily converted into a good leaving group, and W, n, m, $Q_1$ and $Q_2$ are as defined above, with the compounds of formula V and formula VI,

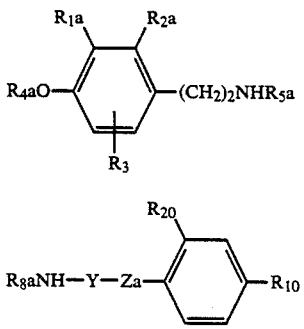

in any order, wherein $R_{1a}$, $R_{2a}$, $R_3$, $R_{4a}$, $R_{5a}$, $R_{8a}$, $R_{10}$, $R_{20}$, Y, and Za are as defined above.

Good leaving groups that $L_1$ and $L_2$ may represent include, for example, halogen, e.g. chlorine or bromine; 1-imidazolyl, trifluoromethanesulph-onate; alkyl carbonate, e.g. ethyl carbonate, benzyl carbonate; alkanoyloxy, e.g. acetoxy, or trifluorocetoxy.

The displacement reactions may be carried out in a solvent which is inert to the reaction conditions, for example, a chlorinated hydrocarbon, e.g. chloroform, in the presence of a non-nucleophilic base, e.g. triethylamine. The reaction may be carried out at a temperature of from about 0° to 100° C.

The free acids of compound IV, i.e. those compounds in which both $L_1$ represents —OH and $Q_1$, represents CO, and/or both $L_2$ represents —OH and $Q_2$ represents CO may be reacted, e.g. with thionyl chloride, ethyl chloroformate, or N,N'-carbonyldiimidazole to convert the carboxyl groups to a group —COL$_1$ or —COL$_2$ respectively. When $L_1$ and/or $L_2$ represent a group which may be converted into a good leaving group, such convertible groups include alkoxy, e.g. ethoxy or methoxy; and hydroxy. The conversion may be effected using conventional techniques.

An example of a sequential replacement of $L_1$ and $L_2$ is as follows:

A compound of formula IV in which $L_1$ represents $OCH_3$, $L_2$ represents OH and both $Q_1$ and $Q_2$ represent CO is reacted with a compound of formula VI in dichloromethane, at 0° C. with N,N'-carbonyldiimidazole, to give the compound of formula VII,

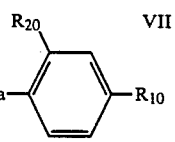

in which $L_1$ represents $OCH_3$, and $R_{8a}$, $R_{10}$, $R_{20}$, m, W, Y, and Za are as defined above:

Saponification of the —COL$_1$ with one equivalent of base, followed by acidification gives the corresponding compound of formula VII with $L_1$ representing —OH, which can be reacted with the appropriate compound of formula V in the presence of N,N'-carbonyldiimidazole to give the desired compound of formula III.

Using analogous processes, the following compounds may be produced:

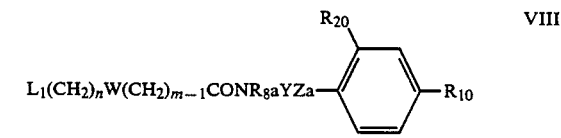

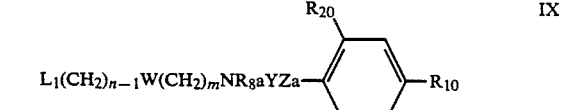

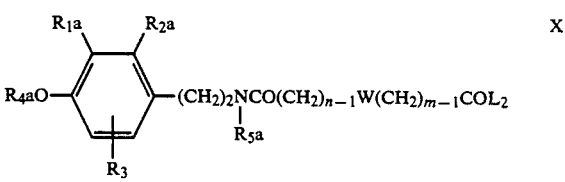

-continued

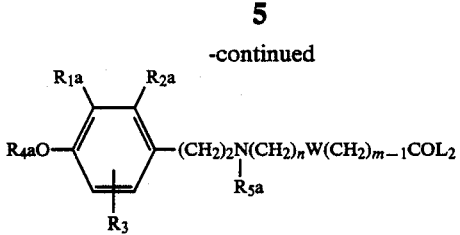

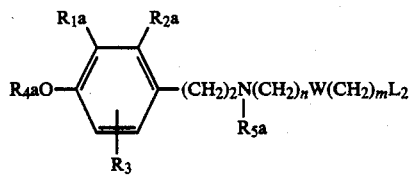

in which $R_{1a}$, $R_{2a}$, $R_3$, $R_{4a}$, $R_{5a}$, $R_{8a}$, $R_{10}$, $R_{20}$, $L_1$, $L_2$, n, m, W, Y, and Za are as defined above.

Similarly, compounds of formula II in which Xa represents $CH_2$ may be made by reacting a compound of formula XIII,

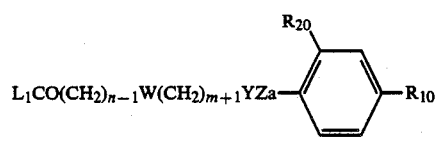

in which $R_{10}$, $R_{20}$, $L_1$, n, m, W, Y, and Za are as defined above, with an appropriate compound of formula V. For example, with $L_1$ representing OH, the compound of formula XIII may be reacted with the compound of formula V to give a compound of formula II in the presence of N,N'-carbonyldiimidazole.

Compounds of formula II may also be made by reacting a corresponding compound of formula XIV,

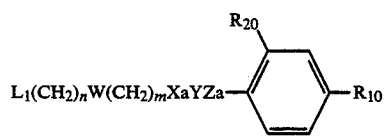

in which $R_{10}$, $R_{20}$, n, m, W, Xa, Y, Za and $L_1$ are as defined above.

with a compound of formula V as defined above.

The reaction is preferably carried out in the presence of a base. As a specific example, $L_1$ may represent bromine, $R_{5a}$ may represent trifluoroacetyl the reaction being carried out in dimethylformamide in the presence of sodium hydride.

Compounds of formula XIV in which Xa represents S or O may be made by reacting a compound of formula XV,

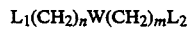

in which $L_1$, $L_2$, n, m, and W are as defined above, with a compound of formula XVI,

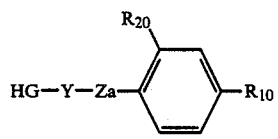

in which G represents O or S and $R_{10}$, $R_{20}$, Y and Za are as defined above.

The reaction is preferably carried out in the presence of a base, e.g. sodium hydride, in an aprotic, polar solvent, e.g. dimethgylformamide.

Compounds of formula II in which Xa represents S or O may also be prepared by reacting the corresponding compound of formula XII as defined above with a compound of formula XVI as defined above, preferably in the presence of a base, e.g. sodium hydride, in an inert solvent, e.g. a polar, aprotic solvent such as dimethylformamide.

Compounds of formula II, in which Xa and Z each represent NH and Y represents CO may be prepared by reacting a compound of formula XVII,

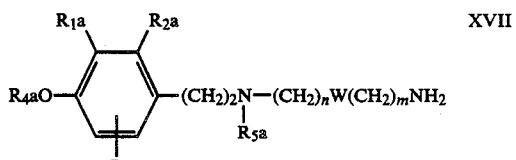

in which $R_{1a}$, $R_{2a}$, $R_3$, $R_{4a}$, $R_{5a}$, n, m and W are as defined above,
with a compound of formula XVIII,

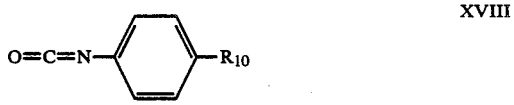

in which $R_{10}$ is as defined above.

The reaction may be carried out in an inert solvent, e.g. toluene at a temperature of from about 0° to 100° C. or in the absence of a solvent.

Compounds of formula XVII may be made from compounds of formula XI, e.g. by conversion of $L_2$ from —$OCH_3$ to —OH to $NH_2$, followed by reduction of the —CO— group by conventional techniques.

Compounds of formula II in which Xa represents NH, Y represents CO and Za represents $CH_2$ or a single bond may be prepared by reacting a compound of formula XVII as defined above with a compound of formula XIX,

in which $Z_b$ represents $CH_2$ or a single bond and $L_1$ and $R_{10}$ are as defined above. The reaction is preferably carried out in the presence of a non-nucleophilic base, e.g. triethylamine, in a solvent which is inert to the reaction conditions, e.g. dichloromethane.

Compounds of formula II in which one or more of Xa, Y or Za represent $SO_2$ may be prepared by selectively oxidizing the corresponding compound of formula II in which Xa, Y or Za represents S. Suitable oxidizing agents include inorganic and preferably organic peracids, e.g. m-chloroperbenzoic acid. The oxidations may be carried out in a solvent inert to the reaction conditions, e.g. dichloromethane, at a temperature of from 0° to 100° C.

Compounds of formula II, in which Xa represents —CONH or —COO may be prepared by reacting the corresponding compound of formula XX,

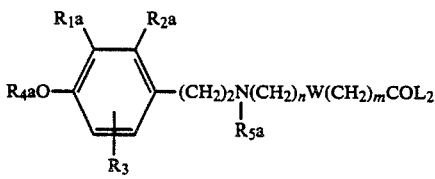

XX in which $R_{1a}$, $R_{2a}$, $R_3$, $R_{4a}$, $R_{5a}$, n, m, $L_2$ and W are as defined above,
with a compound of formula XXI,

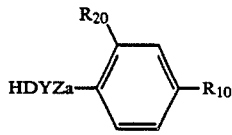

XXI in which D represents O or NH, and $R_{10}$, $R_{20}$, Y and Za are as defined above.

The reaction is preferably carried out by in situ conversion of a compound of formula XX in which $L_2$ represents —OH to an activated mixed anhydride by reaction with, e.g. ethyl chloroformate in the presence of base, followed by reaction with the compound of formula XXI to produce the compound of formula II. The reaction is preferably carried out in solvent inert to the reaction conditions, for example dichloromethane.

The compounds of formula XXI may be prepared by methods analogous to those described above for the compounds of formula XI.

The remaining compounds of formula V, and the compounds of formulae IV, VI, XV, XVI, XVIII, XIX, and XXII, are either known or may be made from known compounds by conventional techniques, known per se.

The acid addition salts of the compounds of formula I may be prepared by reaction of the free-base with an appropriate acid. The acid addition salts may be converted to the corresponding free-base by the action of a stronger base.

The processes as described above may produce the compound of formula I or a derivative thereof. It is also within the scope of this invention to treat any derivative so produced to liberate the free compound of formula I, or to convert one derivative into another.

The compounds of formula I and the intermediates therefor may be isolated from their reaction mixtures using conventional techniques.

Pharmaceutically acceptable derivatives of the compounds of formula I include pharmaceutically acceptable acid addition salts Suitable salts include salts of mineral acids, for example, hydraulic acids, e.g. hydrochloric acid or hydrobromic acid; or organic acids, e.g. formic, acetic or lactic acids. The acid may be polybasic, for example sulfuric, fumaric or citric acid.

Other pharmaceutically acceptable derivatives are compounds which will be suitable bioprecursors (pro-drugs) of the compounds of formula I and will be readily apparent to those skilled in the art and may be made from the compounds of formula I using conventional processes known per se or by processes analogous to those described above Suitable bioprecursors include amides, e.g. acetamides or benzamides, of compounds of formula I, and esters, for example, carboxylic acid esters, e.g. alkanoyl, such as acetyl or isobutyryl, or aroyl C7-9, e.g. benzoyl, esters.

As a preferred group of compounds, we provide the compounds of formula I in which
$R_2$ and $R_3$, which may be the same or different, each independently represent hydrogen, fluorine, chlorine, bromine, alkyl C1 to 6, nitrile, phenyl $(CH_2)_p R_9$ or $SR_9$,
W and Z each represent a single bond,
X represents NH,
Y represents $(CH_2)_q$,
$R_{20}$ represents hydrogen, and
$R_1$, $R_9$, $R_{10}$, n, m, p and q are as first defined above,
and pharmaceutically acceptable derivatives thereof.

As a second preferred group of compounds, we provide the compounds of formula I in which
$R_2$, $R_3$ and $R_{20}$ each represent hydrogen,
W represents a 1,2; 1,3; or 1,4-disubstituted benzene ring, a —CH=CH— group or a 1,4-cyclohexanediyl group;
X represents NH,
Y represents $(CH_2)_q$,
Z represents a single bond, and
n, m, q, $R_1$ and $R_{10}$ are as first defined above,
and pharmaceutically acceptable derivatives thereof.

As a third preferred group of compounds, we provide the compounds of formula I in which
$R_2$, $R_3$ and $R_{20}$ each represent hydrogen,
W and Z each represent a single bond,
X represents O, S, $SO_2$, CO or $CH_2$,
Y represents $(CH_2)_q$, and
$R_1$, $R_{10}$, n, m and q are as first defined above,
and pharmaceutically acceptable derivatives thereof.

As a fourth preferred group of compounds, we provide the compounds of formula I in which
$R_2$, $R_3$ and $R_{20}$ each represent hydrogen,
W represents a single bond,
X represents NH,
Y represents CO, CS or $SO_2$,
Z represents NH or $CH_2$, and
$R_1$, $R_{10}$, n and m are as first defined above,
and pharmaceutically acceptable derivatives thereof As a fifth preferred group of compounds, we provide the compounds of formula I in which,
$R_2$ and $R_3$ each represent hydrogen,
W and Z each represent a single bond,
X represents NH,
Y represents $CR_{15}R_{16}CR_{17}R_{18}$, and
$R_1$, $R_{10}$, $R_{15}$, $R_{16}$, $R_{17}$, $R_{18}$, n and m are as first defined above,
and pharmaceutically acceptable derivatives thereof.

As a sixth preferred group of compounds, we provide the compounds of formula I in which
$R_2$, $R_3$ and $R_{20}$ each represent hydrogen,
W represents a single bond,
X represents NH,
Y represents $(CH_2)_q$,
Z represents O, CO, S, $SO_2$ or $NR_{19}$, and
$R_1$, $R_{10}$, $R_{19}$, n, m and q are as first defined above,
and pharmaceutically acceptable derivatives thereof.

As a seventh preferred group of compounds, we provide the compounds of formula I in which,
$R_2$, $R_3$ and $R_{20}$ each represent hydrogen,
W and Z each represent a single bond,
X represents CONH or COO,
Y represents $(CH_2)_q$, and
$R_1$, $R_{10}$, n, m and q are as first defined above, and pharmaceutically acceptable derivatives thereof $R_2$, $R_3$, $R_{15}$, $R_{16}$, $R_{17}$, $R_{18}$, or $R_{19}$ when they represent alkyl C1 to 6 preferably contain up to and including four carbon atoms. Specific groups that $R_2$, $R_3$, $R_{15}$, $R_{16}$, $R_{17}$, $R_{18}$ or $R_{19}$ may represent include methyl, ethyl, n-propyl, isopropyl and tert-butyl.

We prefer $R_2$ and $R_3$ to be selected from hydrogen, fluorine, chlorine, bromine, $CH_2CH_2C_6H_5$ and $CH_2CH_2C_6H_4OH$. We particularly prefer compounds in which $R_1$ is OH, $R_2$ represents chlorine and $R_3$ represents hydrogen. We also particularly prefer compounds in which $R_1$ is OH and $R_3$ represents fluoro.

We prefer compounds in which W represents a single bond.

We prefer compounds in which X represents NH. We also prefer compounds in which X represents O or S.

Y preferably represents $(CH_2)_q$. We also prefer compounds in which Y represents $CR_{15}R_{16}CR_{17}R_{18}$. We particularly prefer compounds in which

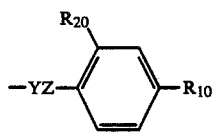

represents 2-indanyl.

Z preferably represents a single bond.

n and m each independently preferably represent 1, 2 or 3.

q preferably represents 1 or 2.

p preferably represents 0, 1 or 2.

When Z represents a single bond, we prefer the sum of n+m to be from 5 to 7 inclusive, especially 6.

The compounds of formula I, and pharmaceutically acceptable derivatives thereof, are useful because they possess pharmacological activity in animals. Thus the compounds act on peripheral and/or central dopamine receptors. As such, they lower blood pressure, reduce heart rate and increase blood flow to certain vascular beds, e.g. renal beds. Some compounds also have an action on other adrenoreceptors, and these exhibit cardiac stimulant and bronchodilator effects. Activity of the compounds has been observed in the following assay systems:

(a) canine renal blood flow, McNay and Goldberg, J. Pharmac, Exp. Ther., 151, 23–31, 1966.

(b) rabbit isolated ear artery, McCullogh, Rand and Story, Br. J. Pharmac, 49, 141–142, 1973, and (c) cat nictitating membrane, Gyorgy and Doda, Arch. Int. Pharmacodyn, 226, 194–206, 1977.

The compounds of the invention are indicated for use in the treatment of congestive heart failure, renal failure, angina pectoris, ischaemic heart disease, hypertension and reversible obstructive airways disease, hyperprolactinaemia and also in Parkinson's disease and other neurological disorders. Compounds of the invention are also indicated for use in the treatment of glaucoma, gastric hypersecretion, e.g. in peptic ulcers, premature labour, acromegaly, and improvement of the blood supply to and healing of intestinal anastomoses and stomata.

The dosage administered will naturally depend on the compound employed, the mode of administration and the desired effect. However, in general, satisfactory results are obtained when the compounds are administered at a dosage of from 0.05 μg to 50 mg per kilogram of body weight per day. For man, the indicated total daily dosage is in the range 2.5 μg to 3.5 g, which may be administered in divided doses of, for example 1 μg to 750 mg.

The new compounds of the present invention may be used in combination with, or sequentially with, a wide variety of other pharmaceutically active substances Where appropriate the compounds may be mixed with one or more other active substances The particular mixture or dose regimen used, and ratio of the active ingredients will depend on a variety of factors including the condition to be treated, the mode of administration, the particular active ingredients and the patient concerned Examples of compounds with which the present compounds may be mixed include:

beta-blockers, especially cardioselective beta blockers, for example, atenolol;

diuretics, for example thiazides, e.g. furosemide;

angiotensin converting enzyme inhibitors, for example captopril;

inotropic agents, for example, amrinone;

antiemetics, for example, sulpiride, metoclopramide, or domperidone.

The compounds of formula I, and pharmaceutically acceptable derivatives thereof, have the advantage that they are more efficacious or produce less undesirable side effects in certain pharmacological models, or are longer acting than compounds of similar structure to the compounds of formula I.

The compounds of the invention may be administered by a wide variety of routes and may act systemically or locally. Thus the compounds may be administered by oral or nasal inhalation to the lung, to the buccal cavity, oesophageally, rectally, topically to the skin or to other available surfaces of the body, e g the eye, by injection, e.g. intravenously, intramuscularly, intraperitoneally, by installation or by surgical implant According to our invention we also provide a pharmaceutical composition comprising preferably less than 80%, and more preferably less than 50%, by weight of a compound of formula I, or a pharmaceutically acceptable derivative thereof, in admixture with a pharmaceutically acceptable adjuvant, diluent or carrier Examples of suitable adjuvants, diluents or carriers are: for tablets, capsules and degrees; microcrystalline cellulose, calcium phosphate, diatomaceous earth, a sugar such as lactose, dextrose or mannitol, talc, stearic acid, starch, sodium bicarbonate and/or gelatin;

for suppositories; natural or hardened oil or waxes; and for inhalation compositions, coarse lactose When the compounds are to be used in aqueous solution it may be necessary to incorporate a chelating or sequestering agent, e.g sodium edetate, an antioxidant, e.g. sodium metabisulphite or buffering agents, e.g. sodium hydrogen phosphate and sodium phosphate. Aqueous solutions typically contain up to about 10% w/w of the new compound and may be used for intravenous injections.

According to the invention, we further provide a method of increasing the force of contraction of the heart in an animal, either human or non-human, which method comprises administering to the animal an effective amount of one or more compounds of the invention.

The invention is illustrated, but in no way limited by the following Examples in which temperatures are in degrees Centigrade.

In general all compounds and intermediates are named in accord with "Naming and Indexing of Chemical substances for Chemical Abstracts", reprinted from Appendix IV of the Chemical Abstracts 1977 Index Guide.

In particular derivatives of hexanedioic acid, in which the carboxylic acid groups are in a 1,6-relation to one another, are named as hexanedioates, not 1,6-hexanedioates.

EXAMPLE 1

5-[2-(6-(2-Phenylethylamino)hexylamino)ethyl]-3-propyl-1,2benzenediol (a) 3,4-Dimethoxy-5-propylbenzenemethanol A solution of 3,4-dimethoxy-5-propylbenzaldehyde (11 g) and sodium borohydride (2 g) in 2-propanol (100 ml) was stirred at room temperature for 2 hours. The mixture was quenched with 2N HCl (200 ml) and extracted with ethyl acetate. The organic phase was separated, washed with brine, dried over MgSO4, filtered and evaporated to leave a yellow oil which was purified by Kugelrohr bulb to bulb distillation at 1 mm Hg air bath temperature 150° to give the sub-title compound as a colorless oil (8 g).

The following compounds were prepared by the method of (a) above:
(i) 3,4-Dimethoxy-2-propylbenzenemethanol; mp, 70°–71.5°;
(ii) 2-Fluoro-4,5-dimethoxybenzenemethanol; ms; m/e 186;
(iii) 2-Fluoro-3,4-dimethoxybenzenemethanol; ms; m/e 186;

(b) 3,4-Dimethoxy-5-propylbenzeneacetonitrile

A solution of the alcohol from step (a) (7.89 g) and thionyl chloride (5.5 ml) in dry dichloromethane was heated under reflux for 2 hours. The solution was evaporated to dryness.

A solution of the crude chloride in dry dimethylsulphoxide (20 ml) was added to a suspension of sodium cyanide (3.68 g) in dry dimethylsulphoxide (20 ml). The mixture was stirred at 20° for 18 hours then quenched with water (100 ml) and extracted with ethyl acetate. The organic phase was washed with brine, dried over magnesium sulphate and evaporated on a steam bath until HCN had ceased to be evolved. Further evaporation gave an oil which was purified by Kugelrohr distillation at 1 mm Hg and air bath temperature 200° to give the sub-title compound as a pale yellow oil (7.3 g).

The following compounds were prepared by the method of 1 (b):
(i) 3,4-Dimethoxy-2-propylbenzeneacetonitrile; mp, 75°–76°;
(ii) 3,4-Dimethoxy-5-nitrobenzeneacetonitrile; MS m/e 222;
(iii) 3,4-Dimethoxy-2-[2-phenylethyl]benzeneacetonitrile; Bp 200° 1 mm Hg;
(iv) 2-Ethyl-3,4-dimethoxybenzeneacetonitrile; Bp 170° 0.5 mm Hg;
(v) 2-Butyl-3,4-dimethoxybenzeneacetonitrile; mp 43°–44°;
(vi) 3,4-Dimethoxy-2-[1-methylethyl]benzeneacetonitrile; Bp 200°/0.35 mm Hg;
(vii) 5,6-Dimethoxy-[1,1'-biphenyl]-2-acetonitrile; Bp 200°/0.5 mm Hg;
(viii) 3,4-Dimethoxy-2-phenylmethylbenzeneacetonitrile; Bp 200°/0.25 mg Hg;
(ix) 3,4-Dimethoxy-2-phenylthiobenzeneacetonitrile; mp 79–80;
(x) 4',5,6-Trimethoxy-[1,1'-biphenyl]-2-acetonitrile; mp 105°–106°;
(xi) 2-[2-[4-Methoxyphenyl]ethyl]-3,4-dimethoxybenzeneacetonitrile; mp 91°–93°;
(xii) 5-Fluoro-3,4-dimethoxy-2-propylbenzeneacetonitrile; Bp 150°/0.2 mm Hg;
(xiii) 3-Fluoro-4,5-dimethoxybenzeneacetonitrile; MS m/e 195;
(xiv) 2-Fluoro-4,5-dimethoxybenzeneacetonitrile; mp 116.3°–117.5°;

(c) 3,4-Dimethoxy-5-propylbenzeneethanamine hydrochloride

A solution of the nitrile from step (b) (8.76 g) in dry tetrahydrofuran (100 ml) was stirred under an atmosphere of nitrogen during the addition of an 1M solution of borane in tetrahydrofuran (120 ml). The solution was heated under reflux for 18 hours. Methanol (100 ml) was added to the cooled reaction mixture and the solution evaporated to dryness. The residue was dissolved in methanolic/HCl (100 ml) and heated under reflux for 4 hours. The solution was evaporated and the solid crystallised from ethyl acetate/cyclohexane as colourless prisms (5.3 g) mp 116°–117°.

The following compounds were prepared by the method of (c):
(i) 3,4-Dimethoxy-2-propylbenzeneethanamine hydrochloride; mp 221°–223°;
(ii) 3,4-Dimethoxy-2-nitrobenzeneethanamine hydrochloride; mp 179.8°–181.8°;
(iii) 3,4-Dimethoxy-5-nitrobenzeneethanamine hydrochloride; mp 179.3°–181.3°;
(iv) 3,4-Dimethoxy-2-(2-phenylethyl)benzeneethanamine hydrochloride; mp 201°–203°;
(v) 2-Ethyl-3,4-dimethoxybenzeneethanamine hydrochloride; mp 253°–255°;
(vi) 2-Butyl-3,4-dimethoxybenzeneethanamine hydrochloride; mp 136°–137°;
(vii) 3,4-Dimethoxy-2-[1-methylethyl]benzeneethanamine hydrochloride; mp 193.9°–195.2°;
(viii) 5,6-Dimethoxy-[1,1'-biphenyl]-2-ethanamine hydrochloride: mp 218°–219°;
(ix) 3,4-Dimethoxy-2-(phenylmethyl)benzeneethanamine hydrochloride; mp 143.3°–144.6°;
(x) 3,4-Dimethoxy-2-(phenylthio)benzeneethanamine hydrochloride; mp 106°–108°;
(xi) 4',5,6-Trimethoxy-[1,1'-biphenyl]-2-ethanamine hydrochloride; mp 177°–178°;
(xii) 2-[2-[4-Methoxyphenyl]ethyl]-3,4-dimethoxybenzene ethanamine hydrochloride; mp 135°–137°;
(xiii) 2-Fluoro-4,5-dimethoxybenzeneethanamine hydrochloride; mp 158°–160°;
(xiv) 3-Fluoro-4,5-dimethoxybenzeneethanamine hydrochloride; mp 161.7°–163.0°;
(xv) 5-Fluoro-3,4-dimethoxy-2-propylbenzeneethanamine hydrochloride; mp 232.7°–234.0°;

(d)
N-[2-(3,4-Dimethoxy-5-propylphenyl)ethyl]-N'-[2phenylethyl]hexanediamide

A solution of 6-oxo-6-(2-phenylethylamino)hexanoic acid (2.05 g) and N,N'-carbonyldiimidazole (1.33 g) in dry dichloromethane (50 ml) was stirred at 20° for 1.5 hours and a solution of 3,4-Dimethoxy-5-propylbenzenethanamine (1.8 g) in dichloromethane (20 ml) then added. The mixture was stirred at 20° for 18 hours and water (50 ml) added. The organic phase was separated, washed with dilute hydrochloric acid, aqueous sodium bicarbonate and brine, dried over MgSO$_4$ and evaporated to leave a colourless solid. Crystallisation from 2-propanol/cyclohexane gave the bis amide as colorless prisms (2.7 g) mp 128°–129°.

The following compounds were prepared by the method of 1 (d):

(i) N-[2-(3,4-Dimethoxy-2-propylph-enyl)ethyl]-N'-[2phenylethyl]hexanediamide; mp 137.8°–138.5°;

(ii) N-[2-(3,4-Dimethoxy-2-methylphenyl)ethyl]-N'-[2phenylethyl]hexanediamide; mp 165°–167°;

(iii) N-[2-(3,4-Dimethoxy-2-nitrophenyl)ethyl]-N'-[2phenylethyl]hexanediamide; mp 143.2°–144.5°;

(iv) N-[2-(3,4-Dimethoxy-5-nitrophenyl)ethyl]-N'-[2phenylethyl]hexanediamide; mp 154.8°–156°;

(v) N-[2-(2-Chloro-3,4-dimethoxyphenyl)ethyl]-N'-[2-phenylethyl]hexanediamide; mp 162°–165°;

(vi) N-[2-(3,4-Dimethoxyphenyl)2-methyl]propyl-N'[2-phenylethyl]hexanediamide; mp 94°–96°;

(vii) N-[2-[3,4-Dimethoxy-2-[2-phenylethyl]phenyl]ethyl]-N'-[2-phenylethyl]hexanediamide; mp 158°–160°;

(viii) N-[2-[2-Ethyl-3,4-dimethoxyphenyl]ethyl]-N'-[2-phenylethyl]hexanediamide; mp 154°–156°;

(ix) N-[2-[2-Butyl-3,4-dimethoxyphenyl]ethyl]-N'-[2phenylethyl]hexanediamide; mp 138°–139°;

(x) N-[2-[3,4-Dimethoxy-2-[1-Methylethyl]phenyl]ethyl]-N'[2-phenylethyl]hexanediamide; mp 111.6°–112.8°;

(xi) N-[2-[[1,1'-Biphenyl]-2-yl-5,6-dimethoxy]ethyl]-N'[2-phenylethyl]hexanediamide; mp 146°–147°;

(xii) N-[2-[2,3,4-Trimethoxyphenyl]ethyl]-N'-[2phenylethyl]hexanediamide; mp 127°–129°;

(xiii) N-[2-[3,4-Dimethoxy-2-(phenylmethyl)phenyl]ethyl]-N'[2-phenylethyl]hexanediamide; mp 137.8°–138.6°;

(xiv) N-[2-[3,4-Dimethoxy-2-(phenylthio)phenyl]ethyl]-N'[2-phenylethyl]hexanediamide; mp 137.6°–138.°;

(xv) N-[2-[[1,1'-Biphenyl]-2-yl-4',5,6-trimethoxy]ethyl]-N'-[2-phenylethyl]hexanediamide; mp 187°–189°;

(xvi) N-[2-[2-[2-[4-methoxyphenyl]ethyl]-3,4dimethoxyphenyl]ethyl]-N'-[2-phenylethyl]hexane diamide; mp 152°–154°;

(xvii) N-[2-[2-Fluoro-3,4-dimethoxyphenyl]ethyl]-N'-[2-phenylethyl]hexanediamide; mp 142°–143°;

(xviii) N-[2-[2-Bromo-3,4-dimethyoxphenyl]ethyl]-N'[2-phenylethyl]hexanediamide; mp 176°–178°;

(xix) N-[2-[2-Fluoro-4,5-dimethoxyphenyl]ethyl]-N'[2-phenylethyl]hexanediamide; mp 142°–143°

(xx) N-[2-[4,5-Dimethoxy-2-methylphenyl]ethyl]-N'[2-phenylethyl]hexanediamide; mp 146°–147°;

(xxi) N-[2-[3-Fluoro-4,5-dimethoxyphenyl]ethyl]-N'[2-phenylethyl]hexanediamide; mp 149°–150°;

(xxii) N-[2-[3-Chloro-4,5-dimethoxyphenyl]ethyl]-N'[2-phenylethyl]hexanediamide; mp 148.8°–150.2°;

(xxiii) N-[2-[3-Bromo-4,5-dimethoxyphenyl]ethyl]-N'[2-phenylethyl]hexanediamide; mp 150.4°–152°;

(xxiv) N-[2-[3,4-Dimethoxy-5-methylphenyl]ethyl]-N'[2-phenylethyl]hexanediamide; mp 136.7°–137.7°;

(xxv) N-[2-[5-Fluoro-3,4-dimethoxy-2-propylphenyl]ethyl]-N'-[2-phenylethyl]hexanediamide; mp 122.6°–123.9°;

(e)
N-[2-(3,4-Dimethoxy-5-propylphenyl)ethyl]-N'-[2phenylethyl]-1,6-hexanediamine A solution of the bis amide product from step (d) (2.27 g) in dry tetrahydrofuran (100 ml) was stirred under a nitrogen atmosphere while borane in tetrahydrofuran (25 ml of a 1M solution) was added. The solution was heated under reflux for 24 hours.

Methanol (100 ml) was added to the cooled solution and the mixture evaporated to dryness. The residue was dissolved in methanolic HCl (100 ml) and heated under reflux for 2 hours. The solution was evaporated and the sub-title compound as the dihydrochloride salt crystallised from ethanol as colorless prisms (1.9 g) mp 222°–224°.

The following compounds were prepared by the method of (e):

(i) N-[2-(3,4-Dimethoxy-2-propylphenyl)ethyl]-N'-[2-phenylethyl]-1,6-hexanediamine dihydrochloride; mp 224°–225.5°;

(ii) N-[2-(3,4-Dimethoxy-2-methylphenyl)ethyl]-N'-[2phenylethyl]-1,6-hexanediamine dihydrochloride; mp 285°–287° dec;

(iii) N-[2-(3,4-Dimethoxy-2-nitrophenyl)ethyl]-N'-[2-phenylethyl]-1,6-hexanediamine dihydrochloride; mp 215.4°–216.9°;

(iv) N-[2-(3,4-Dimethoxy-5-nitrophenyl)ethyl]-N'-[2-phenylethyl)-1,6-hexanediamine dihydrochloride; mp 213°–215°;

(v) N-[2-(2-Chloro-3,4-dimethoxyphenyl)ethyl]-N'-[2phenylethyl]-1,6-hexanediamine dihydrochloride; mp 269°–272°;

(vi) N-[2-[3,4-Dimethoxy-2-[2-phenylethyl]phenyl]ethyl]-N'-[2-phenylethyl]-1,6-hexanediamine dihydrochloride; mp 243°–245 ;

(vii) N-[2-[2-Ethyl-3,4-dimethoxyphenyl]ethyl]-N'-[2phenylethyl]-1,6-hexanediamine dihydrochloride; mp 249°–251°;

(viii) N-[2-[2-Butyl-3,4-dimethoxyphenyl]ethyl]-N'[2-phenylethyl]-1,6-hexanediamine dihydrochloride; mp 209°–211°;

(ix) N-[2-[3,4-Dimethoxy-2-[1-methylethyl]phenyl]ethyl]-N'-[2-phenylethyl]-1,6-hexanediamine dihydrochloride; mp 233°–235°;

(x) N-[2-[[1,1'-Biphenyl]-2-yl-5,6-dimethoxy]ethyl]-N'[2-phenylethyl]-1,6-hexanediamine dihydrochloride; mp 206°–208°;

(xi) N-[2-[2,3,4-Trimethoxyphenyl]ethyl]-N'-[2phenylethyl]-1,6-hexanediamine dihydrochloride; mp 243°–245°;

(xii) N-[2-3,4-Dimethoxy-2-(phenylmethyl)phenyl]ethyl]-N'-[2-phenylethyl]-1,6-hexanediamine dihydrochloride; mp 194°–196°;

(xiii) N-[2-[3,4-Dimethoxy-2-(phenylthio)phenyl]ethyl]-N'-[2-phenylethyl]-1,6-hexanediamine dihydrochloride; mp 180.6°–182°;

(xiv) N-[2-[[1,1'-Biphenyl]-2-yl-4',5,6-trimethoxy]ethyl]-N'-[2-phenylethyl]-1,6-hexanediamine dihydrochloride; mp 236°–238°;

(xv) N-[2-[2-[2-[4-Methoxyphenyl]ethyl]-3,4-dimethyoxy-phenyl]ethyl]-N'-[2-phenylethyl]-1,6-hexane diamine dihydrochloride; mp 221°–223°;

(xvi) N-[2-[2-Fluoro-3,4-dimethyoxyphenyl]ethyl]-N'-[2phenylethyl]-1,6-hexanediamine dihydrochloride; mpt 275°–276° dec;

(xvii) N-[2-[2-Bromo-3,4-dimethoxyphenyl]ethyl]-N'[2-phenylethyl]-1,6-hexanediamine dihydrochloride; mpt 260°-262° dec;

(xviii) N-[2-[2-Fluoro-4,5-dimethyoxyphenyl]ethyl]-N'-[2phenylethyl]-1,6-hexanediamine dihydrochloride; mp 258°-260° dec;

(xvix) N-[2-[4,5-Dimethoxy-2-methyl-phenyl]ethyl]-N'-[2phenylethyl]-1,6-hexanediamine dihydrochloride; mp 221°-223°;

(xx) N-[2-[3-Fluoro-4,5-dimethoxyphenyl]ethyl]-N'-[2phenylethyl]-1,6-hexanediamine dihydrochloride; mp 260.3-262.3;

(xxi) N[2-[3-Chloro-4,5-dimethoxyphenyl]ethyl]-N'-[2phenylethyl]-1,6-hexanediamine dihydrochloride; mp 254-256.5 dec;

(xxii) N-[2-[3-Bromo-4,5-dimethoxyphenyl]ethyl]-N'-[2phenylethyl]-1,6-hexanediamine dihydrochloride; mp 251.6-252.9 dec;

(xxiii) N-[2-[3,4-Dimethoxy-5-methylphenyl]ethyl]-N'-[2phenylethyl]-1,6-hexanediamine dihydrochloride; mp 259°-262°;

(xxiv) N-[2-[5-Fluoro-3,4-dimethoxy-2-propylph-enyl-]ethyl]-N'-[2-phenylethyl]-1,6-hexanediamine dihydrochloride; mp 225.6°-226.8°;

(f)

5-[2-(6-(2-Phenylethylamino)hexylamino)ethyl]-3-propyl-1,2-benzenediol dihydrobromide A solution of the diamine from step (e) (1.7 g) in 48% aqueous hydrobromic acid (20 ml) containing hypophosphorous acid (0.1 ml) was heated under reflux under a nitrogen atmosphere for 4 hours. The solution was evaporated to dryness and the solid crystallised from 2-propanol/ether to give the hydrobromide of the sub-title compound as colorless prisms (1.3 g) mp 151°-152° presoftens 147°.

The following compounds of formula I were prepared by the method of (f):

(i) 4-[2-(6-(2-Phenylethylamino)hexylamino)ethyl]3-propyl-1,2-benzenediol dihydrobromide; mp 95°-97°;

(ii) 3-Methyl-4-[2-(6-(2-phenylethylamino)hexylamino)ethyl]-1,2-benzenediol dihydrobromide; mp 231°-232°;

(iii) 3-Nitro-4-[2-(6-(2-phenylethylamino)hexylamino)ethyl]-1,2-benzenediol dihydrobromide; mp 194.6°-195.1° dec;

(iv) 3-Nitro-5-(2-(6-(2-phenylethylamino)hexylamino)ethyl]-1,2-benzenediol dihydrobromide; mp 245°-247° dec;

(v) 3-Chloro-4-[2-(6-(2-phenylethylamino)hexylamino)ethyl]-1,2-benzenediol dihydrobromide; mp 209°-210°;

(vi) 3-[2-Phenylethyl]-4-[2-[6-[2-phenylethylamino]hexylamino]ethyl]-1,2-benzenediol dihydrobromide; mp 143°-145°;

(vii) 3-Ethyl-4-[2-[6-[2-phenylethylamino]hexylamino]ethyl]-1,2-benzenediol dihydrobromide; mp 178°-180°;

(viii) 3-Butyl-4-[2-[6-[2-phenylethylamino]hexylaminoethyl-1,2-benzenediol dioxalate; mp 198°-200°;

(ix) 6-[2-[6-[2-Phenylethylamino]hexylamino]ethyl]-[1,1'-biphenyl]-2,3-diol dihydrobromide hemihydrate; mp 196°-198°;

(x) 4-[2-[6-[2-Phenylethylamino]hexylamino]ethyl]-1,2,3-benzenetriol dihydrobromide; mp 209°-210°;

(xi) 4-[2-[6-[2-Phenylethylamino]hexylamino]ethyl]-3-phenylmethyl-1,2-benzenediol dihydrobromide; mp 169°-172°;

(xii) 3-[2-[4-Hydroxyphenyl]ethyl]-4-[2-[6-[2-phenyl ethylamino]hexylamino]ethyl]-1,2-benzenediol dihydrobromide; mp 178°-180°;

(xiii) 3-Fluoro-4-[2-[6-[2-phenylethylamino]hexylamino]ethyl]-1,2-benzenediol dihydrobromide; mp 231°-233°;

(xiv) 3-Bromo-4-[2-[6-[2-phenylethylamino]hexylamino]ethyl]-1,2-benzenediol dihydrobromide; mp 207°-208°;

(xv) 5-Fluoro-4-[2-[6-[2-phenylethylamino]hexylamino]-ethyl]-1,2-benzenediol dihydrobromide; mp 218°-220°;

(xvi) 5-Methyl-4-[2-[6-[2-phenylethylamino]hexylamino]ethyl]-1,2-benzenediol dihydrobromide; mp 221°-223°;

(xvii) 3-Fluoro-5-[2-[6-[2-phenylethylamino]hexylamino]ethyl]-1,2-benzenediol dihydrobromide; mp 207.4°-208.4°;

(xviii) 3-Methyl-5-[2-[6-2-phenylethylamino]hexylamino]ethyl]-1,2-benzenediol dihydrobromide; mp 188°-191°;

(xix) 6-Fluoro-4-[2-[6-[2-phenylethylamino]hexylamino]ethyl]-3-propyl-1,2-benzenediol dihydrobromide; mp 192.6°-193.4°.

EXAMPLE 2

3-[1-Methylethyl]-4-[2-[6-[2-phenylethylamino]hexylamino]ethyl]-1,2-benzendiol

A suspension of the bis amine prepared by the process of Example 1 (e) (1.7 g) in dry dichloromethane (50 ml) in a nitrogen atmosphere was cooled to −78°. A 1M solution of boron tribromide in dichloromethane (13.6 ml) was added dropwise and the mixture allowed to stir at room temperature for 2 hours. Methanol (50 ml) was slowly added to the mixture and the solution evaporated to dryness and the solid crystallised from ethanol to give the title compound dihydrobromide salt as colorless prisms (1.24 g); mp 221.8°-229.8°.

EXAMPLE 3

The following compounds of formula I were prepared from the corresponding intermediates of Example 1 (e), by the method of Example 2:

(i) 4-[2-[6-[2-Phenylethylamino]hexylamino]ethyl]-3-phenylthio-1,2-benzenediol dihydrobromide;

(ii) 6-[2-[6-[2-Phenylethylamino]hexylamino]ethyl]-[1,1'-biphenyl]-2,3,4'-triol dihydrobromide; mp 239°-240°;

(iii) 3-Chloro-5-[2-[6-[2-phenylethylamino]hexylamino]ethyl]-1,2-benzenediol dihydrobromide; mp 194.9°-197°;

(iv) 3-Bromo-5-[2-[6-[2-phenylethylamino]hexylamino]ethyl]-1,2-benzenediol dihydrobromide; mp 184°-186°;

EXAMPLE 4

Benzene methanols analogous to those prepared by the process of Example 1 (a) may also be prepared from the following compounds:

(a)
2-[3,4-Dimethoxy-2-(2-phenylethyl)phenyl]-4,5-dihydro-4,4-dimethyloxazole

A solution of phenylethyl magnesium bromide (1M in tetrahydrofuran (40 ml) was added to a stirred solution of 4,5-dihydro 4,4-dimethyl-2-(2,3,4-trimethoxyphenyl) oxazole (5.3 g 0.02M) in dry tetrahydrofuran under a nitrogen atmosphere. The mixture was stirred at 20° for 16 hours. Water (200 ml) was added and the aqueous phase thoroughly extracted with diethyl ether (3×200 ml). The organic solution was dried over magnesium sulphate, filtered and evaporated to leave an oil which was purified by column chromatography on SiO2 eluting with ether/petroleum ether (50/50) to give a colorless oil (6.2 g); MS m/e 339.

Similarly prepared were:
(i) 2-[2-Ethyl-3,4-dimethoxyphenyl]-4,5-dihydro-4,4dimethyloxazole; Bp 170°-180°/1 mm Hg;
(ii) 2-[2-Butyl-3,4-dimethoxyphenyl]-4,5-dihydro-4,4-dimethyloxazole; Bp 170°-180°/0.5 mm Hg;
(iii) 2-[3,4-Dimethoxy-2-[1-methylethyl]phenyl]-4,5-dihydro-4,4-dimethyloxazole; MS; m/e 277;
(iv) 2-[[1,1'-Biphenyl]-2-yl-5,6-dimethoxy]-4,5-dihydro-4,4-dimethyloxazole; mp 107°-108.5°;
(v) 2-[[1,1'-Biphenyl]-4,5,6-trimethoxy-2-yl]-4,5-dihydro-4,4 -dimethyloxazole; MS; m/e 341;
(vi) 4,5-Dihydro-2-[2-[2-[4-methoxyphenyl]ethyl]-3,4-dimet hoxyphenyl]-4,4-dimethyloxazole; MS; m/e 369;
(vii) 2-[2-Bromo-3,4-dimethoxyphenyl]-4,5-dihydro-4,4-dimethyloxazole; mp 60°-62°.

(b)
2-3,4-Dimethoxy-2-phenylmethylphenyl]-4,5-dihydro-4,4-dimethyloxazole

A solution of 2-[3,4-Dimethoxyphenyl]-4,5-dihydro 4,4-dimethyloxazole (15 g) in dry tetrahydrofuran (100 ml) under a nitrogen atmosphere was cooled to −45° in a chlorobenzene/dry ice bath. Butyl lithium (45.9 ml 1.6M solution) was added dropwise and the mixture stirred at −45° for 2 hours. Phenylmethyl bromide (38 ml) was then added dropwise and the mixture allowed to stir at 20° for 16 hours. The mixture was quenched with brine and the aqueous phase extracted with ether. The organic phase was separated, dried over magnesium sulphate, filtered and evaporated to leave a solid. Purification by flash chromatography (30% ether/40/60 petrol) gave the title compound as a colorless solid (10.58 g); mp 81°-82°.

Similarly prepared were:
(i) 2-[3,4-Dimethoxy-2-[phenylthio]phenyl]-4,5-dihydro-4,4-dimethyloxazole MS; m/e 343.

(c) 3,4-Dimethoxy-2-[2-phenylethyl]benzoic acid

A solution of the product from step (a) (6 g) in excess methyl iodide (11.3 ml) was stirred at 20° for 16 hours and heated under reflux for 2 hours. The solution was evaporated and the solid triturated with ether and dried.

A solution of this oxazolinium salt in 20% aqueous sodium hydroxide (200 ml) and methanol (200 ml) was heated under reflux for 16 hours. The solution was evaporated to half volume, cooled and acidified with 2N HCl. The precipitate was filtered, dried and crystallised from cyclohexane as colorless prisms (3.5 g); mp 142°-144°

Similarly prepared from the corresponding product of step (a) or (b) were:

(i) 2-Butyl-3,4-dimethoxybenzoic acid; mp 112°-114°;
(ii) 5,6-Dimethoxy-[1,1'-biphenyl]-2-carboxylic acid; mp 198°-200°;
(iii) 3,4-Dimethoxy-2-(phenylmethyl)benzoic acid; mp 148°-150.5°;
(iv) 3,4-Dimethoxy-2-(phenylthio)benzoic acid; mp 168°-169.8°
(v) 4',5,6-Trimethoxy-[1,1'-biphenyl]-2-carboxylic acid; mp 218°-220°;
(vi) 2-[2-[4-Methoxyphenyl]ethyl]-3,4-dimethoxybenzoic acid; mp 159°-160°;

(d) 3,4-Dimethoxy-2-[2-phenylethyl]benzenemethanol

A 2 Molar solution of borane-tetrahydrofuran complex (12.2 ml) was added to a solution of the product of step (c) (3.5 g) in dry tetrahydrofuran (50 ml) under a nitrogen atmosphere. The solution was heated at reflux for 3 hours, cooled to room temperature, and methanol (50 ml) added. The solution was evaporated to dryness, dissolved in ethyl acetate and washed with dilute hydrochloric acid, saturated sodium bicarbonate solution and water. The organic phase was dried over magnesium sulphate, filtered and evaporated to leave a solid which crystallised from cyclohexane as colorless flakes (3.1 g); mp 99°-100°;

Similarly prepared from the appropriate product of step (c) were:
(i) 2-Ethyl-3,4-dimethoxybenzenemethanol; Bp 150/0.5 mm Hg;
(ii) 2-Butyl-3,4-dimethoxybenzenemethanol; mp 68°-70°;
(iii) 5,6-Dimethoxy-[1,1'-biphenyl]-2-methanol; Bp 170/0.5 mm Hg;
(iv) 3,4-Dimethoxy-2-phenylmethylbenzenemethanol; Bp 200°/0.15 mm Hg;
(v) 3,4-Dimethoxy-2-phenylthiobenzenemethanol; mp 56°-58°;
(vi) 4',5-6-Trimethoxy-[1,1'-biphenyl]-2-methanol; mp 100°-102°;
(vii) 2-[2-[4-Methoxyphenyl]ethyl]-3,4-dimethoxybenzenemethanol; mp 83°-85°;
(viii) 5-Fluoro-3,4-dimethoxy-2-propylbenzenemethanol; MS; m/e 229;

EXAMPLE 5

Benzaldehydes for the process of Example 1(a) may be prepared by the following route:

(a) 3-Acetyloxy-4-methoxy-2-propylbenzaldehyde

A solution of 3-hydroxy-4-methoxy-2propylbenzaldehyde (36.6 g) in dry dimethylformamide (50 ml) was added to a suspension of sodium hydride (4.5 g) in dry dimethylformamide (20 ml) in a nitrogen atmosphere. The mixture was stirred at 20° for 30 mins followed by the addition of acetyl chloride (13.5 ml) dropwise over a period of 15 min. The mixture was stirred at 20° for 24 hours.

The solvent was evaporated and the residue treated with dilute hydrochloric acid. The aqueous phase was extracted with ethyl acetate which was washed with brine, dried, filtered and evaporated to leave a yellow oil (39 g); MS; m/e 236.

(b)
3-Acetyloxy-4-methoxy-5-nitro-2-propylbenzaldehyie

A solution of the product from step (a) (8.8 g) in dry carbon tetrachloride (50 ml) was cooled to −5° during the dropwise addition of fuming nitric acid (19.8 ml)

over a period of 1 hour. The mixture was stirred at 0° for 1 hour and then poured onto ice/water. The aqueous phase was extracted with chloroform which was separated, washed with brine, dried, filtered and evaporated to leave a yellow oil (9.9 g); MS m/e 281.

(c)
3-Hydroxy-4-methoxy-5-nitro-2-propylbenzaldehyde

A suspension of the product from step (b) (39.5 g) in 20% sodium hydroxide solution (140 ml) was heated at 90° for 5 hours. The mixture was cooled and acidified with dilute hydrochloric acid. The aqueous phase was extracted with ethyl acetate washed with brine, dried, filtered and evaporated to leave a brown oil (33 g) MS; m/e 239.

(d) 3,4-Dimethoxy-5-nitro-2-propylbenzaldehyde

A solution of the product from step (c) (40.2 g), potassium carbonate (46.5 g) and methyl iodide (20.9 ml) in dry dimethylformamide (150 ml) was stirred at 20° C. for 16 hours. The solvent was evaporated and the residue quenched with water. The aqueous phase was extracted with ethyl acetate which was washed with brine, dried, filtered and evaporated to leave a yellow oil (27.4 g), MS; m/e 283.

(e)
2,3-Dimethoxy-5-dimethoxymethyl-4-propylnitrobenzene

A solution of the aldehyde from step (d) (14 g) tosic acid (0.2 g) and trimethylorthoformate (6.7 ml) in dry methanol (100 ml) was heated under reflux for 30 mins. A solution of potassium hydroxide in methanol (5 ml) was added to the reaction mixture and the solution evaporated to dryness. The residue was dissolved in ether, washed with water, dried, filtered and evaporated to leave a solid which crystallised from pentane as pale yellow prisms (11.6 g); mp 52.1°–54.0°.

(f) 3,4-Dimethoxy-5-fluoro-2-propylbenzaldehyde

The acetal (11.5 g) from step (e) was hydrogenated at atmospheric pressure in dry ethanol (100 ml) using Adam's catalyst. The catalyst was filtered and the solution was evaporated to give the intermediate amine as a green oil (10.5 g) which was used without further purification.

A solution of the amine (5.1 g) in 40% fluoroboric acid (300 ml) was cooled to −5° during the dropwise addition of a cold solution of sodium nitrite (1.45 g) in water (10 ml). The mixture was stirred at 0° C. for 1 hour.

The solution was then irradiated with a 400 w medium pressure Hg lamp at −10° in a nitrogen atmosphere for 1 hour.

The solution was basified with 40% sodium hydroxide solution and extracted with ethyl acetate. The organic phase was washed with water, dried, filtered and evaporated to leave an oil which was purified by column chromatography (SiO$_2$) eluting with dichloromethane to leave the title aldehyde as a pale yellow oil, MS; m/e 226.

EXAMPLE 6

4-[2-[4-[(2-Phenylethyl)aminomethyl]phenylmethylamino]ethyl]1,2-benzenediol (a) Methyl 4-(2-phenylethylaminocarbonyl)benzoate N,N'-Carbonyldiimidazole (16.2 g, 0.1 mole) was added portionwise under nitrogen to 1,4-benzenedicarboxylic acid monomethyl ester (18 g, 0.1 mole) in dry dichloromethane (250 ml) and stirred for 1 hour. Benzeneethanamine (12.1 g, 0.1 mole) was added and the reaction stirred for 3 hours. The solution was washed with dilute hydrochloric acid, aqueous sodium bicarbonate solution and water, dried and evaporated. The residue, on trituration with ether, afforded the sub-title compound (23.8 g) as a white solid mp 148°.

(b) 4-(2-Phenylethylaminocarbonyl)benzoic acid

The product from step (a) (23.5 g 83 mmoles) was dissolved in refluxing methanol (250 ml) and a solution of sodium hydroxide (6.64 g, 166 mmoles) in water (10 ml) was added. The solid, which separated almost immediately, was filtered off, dissolved in water and acidified. The precipitate was separated, washed with water, dried and triturated with ether to give the sub-title acid (21.1 g) as a white solid mp 237°–238.5°.

(c)
N-[2-(3,4-Dimethoxyphenyl)ethyl]-N'-(2-phenylethyl)-1,4-benzenedicarboxamide The product from step (b) (9.0 g, 33 mmoles) was dissolved in dichloromethane (150 ml) under nitrogen and N,N'-carbonyldiimidazole (5.9 g, 36 mmoles) was added. The solution was stirred for 1 hour and 3,4-dimethoxybenzeneethanamine (5.97 g, 33 mmoles) added in one portion. After stirring for a further 2 hours the precipitated solid was collected, washed with aqueous sodium bicarbonate solution and water and dried giving the sub-title bis amide (7.6 g) mp 223°–225°.

(d)
N-[2-(3,4-Dimethoxyphenyl)ethyl]-N'-(2-phenylethyl)-1,4-benzenebis(methanamine)

Diborane (1M solution in tetrahydrofuran, 82.5 ml, 82.5 mmoles) was added to the product from step (c) (7.2 g, 16.7 mmoles) in dry tetrahydrofuran (500 ml) under nitrogen and the resulting mixture heated under reflux for 5 hours, then cooled and treated cautiously with dry methanol. Excess saturated methanolic hydrogen chloride was added and the solution was stirred overnight at 20°. The solid produced was filtered, washed with ether and dried giving the sub-title compound as the dihydrochloride salt (6.9 g) mp > 250°.

(e)
4-[2-[4-[(2-Phenylethyl)aminomethyl]phenylmethylamino]ethyl]-1,2-benzenediol dihydrobromide The hydrochloride product from step (d) (6.0 g, 12.6 mmoles) in 48% hydrobromic acid (100 ml) containing hypophosphorous acid (0.5 ml) was boiled under reflux under nitrogen for 4 hours. The precipitate which formed on cooling the solution was filtered off and recrystallised from aqueous ethanol giving the title compound as the dihydrobromide salt, white crystals (2.6 g) mp > 250°.

EXAMPLE 7

4-[2-[4-[(2-Phenylethyl)aminomethyl]-trans cyclohexylmethylamino]ethyl]-1,2-benzenediol (a)
Methyl-trans-4-(2-phenylethylaminocarbonyl)cyclohexanecarboxylate The product was prepared from benzeneethanamine and 1,4-trans cyclohexanedicarboxylic acid monomethyl ester by the method described in Example 6 (a) mp 120°–124°.

(b) Trans-4-(2-phenylethylaminocarbonyl)cyclohexane carboxylic acid

This was prepared from the product of step (a) by the method of Example 6 (b) mp 124°–126°.

(c) N-[2-(3,4-Dimethoxyphenyl)ethyl]-N'-(2-phenylethyl) trans-1,4-cyclohexanedicarboxamide This was prepared from the product of step (b) by the method of Example 6 (c) mp>250°.

(d) N-[2-(3,4-Dimethoxyphenyl)ethyl]-N'-(2-phenylethyl) trans-1,4-cyclohexanebis(methanamine) dihydrochloride This was prepared from the product of step (c) by the method of Example 6 (d) mp 325°–327° (dec).

(e) 4-[2-[4-[(2-Phenylethyl)aminomethyl]-transcyclohexylmethylamino]ethyl]-1,2-benzenediol dihydrobromide This was prepared from the product of step (d) by the method of Example 6 (e) mp 321° (dec).

EXAMPLE 8

4-[2-[2-[2-[2-(2-Phenylethyl)aminoethyl]phenyl]ethyl]amino]ethyl]-1,2-benzenediol (a) Methyl 2-[2-phenylethylaminocarbonyl methyl]benzene acetate This was prepared from benzeneethanamine and 1,2-benzenediacetic acid monomethyl ester by the method described in Example 6(a), MS;$m/e$ 311.

(b) 2-[2-Phenylethyl aminocarbonyl methyl]benzeneacetic acid

This was prepared by the method of Example 6(b) from the product of step (a), MS;$m/e$ 297.

(c) N-[2-(3,4-Dimethoxyphenyl)ethyl]-N'-(2-phenylethyl)-1,2-benzenediacetamide

This was prepared by the method of Example 6 (c) from the product of step (b) mp 149°–151°.

(d) N-[2-(3,4-Dimethoxyphenyl)ethyl]-N'-(2-phenylethyl)-1,2-benzenediethanamine dihydrochloride This was prepared by the method of Example 6(d) from the product of step (c) mp 270°–272°.

(e) 4-[2-[2-[2-[2-(2-Phenylethyl)aminoethyl]phenyl]ethyl]aminoethyl]-1,2-benzenediol dihydrobromide This was prepared by the method of Example 6(e) from the product of step (d), mp 291°–293°.

EXAMPLE 9

4-2-[3-[2-[2-(2-Phenylethylaminomethyl)phenyl]-propylamino]ethyl]-1,2-benzenediol (a) Methyl 2-carboxybenzenepropanoate 2-carboxybenzenepropanoic acid (9.7 g., 0.05 mole), acetic anhydride (15.5 g., 0.15 mole) and acetyl chloride (0.5 g) in dichloromethane (200 ml) was boiled at reflux under nitrogen for 16 hr. The solvents were removed at high vacuum and the residual cyclic anhydride was heated at reflux with methanol (250 ml) for 2 hrs. Evaporation of solvent gave the sub-title compound as an oil which crystallised with petroleum ether (b.p.60°–80°) to a solid (6.3 g) mp 76°–79°. This was further purified by continuous extraction of the crude product with boiling petroleum (b.p.40°–60°) in a Soxhlet apparatus. The pure compound, mp 79°–81° separated from the extracts on cooling.

(b) Methyl 2-(2-phenylethylaminocarbonyl)benzenepropanoate

The sub-title compound was prepared from benzeneethanamine and the product of step (a) using the method of Example 6(a) as a white solid mp 68°–70°.

(c) 2-(2-Phenylethylaminocarbonyl)benzenepropanoic acid

The sub-title compound was prepared from the product of step (b) using the procedure of Example 6(b) mp 106°–8°.

(d) N-[2-(3,4-Dimethoxyphenyl)ethyl]-2-(2-phenylethylaminocarbonyl)benzenepropanamide This was prepared from the product of step (c) and 3,4-dimethoxybenzeneethanamine using the procedure of Example 6(c) mp 122°–3°.

(e) N-[2-(3,4-Dimethoxyphenyl)ethyl]-2-(2-phenylethyl aminomethyl)benzenepropanamine dihydrochloride Acetic acid (2.65 g., 44 mmoles) in dry dioxan (35 ml) was added dropwise to a stirred solution of the product of step (d) above (4.0 g., 8.8 mmoles) and sodium borohydride (1.66 g., 43.8 mmoles) in dry dioxan (90 ml) under nitrogen. The mixture was heated at reflux for 24 hr. then evaporated to dryness. The residue was partitioned between water and chloroform, the organic layer evaporated and the residue was dissolved in saturated methanolic hydrogen chloride. Evaporation of the methanol and recrystallisation of the residue from 2-propanol gave the sub-title compound as white crystals (1.4 g) mp 206°–8°.

(f) 4-[2-[-3-[2-(2-Phenylethylaminomethyl)phenyl]-propylamino]ethyl]-1,2-benzenediol dihydrobromide This was prepared from the product of step (e) using the procedure of Example 6(e). The title compound crystallised from 2-propanol as a solvate, mp 196°–8° (dec) containing 1 mole of 2-propanol. This could not be removed by conventional drying techniques, but repeated evaporation of a methanol solution in vacuo eventually gave solvent-free title compound mp 295° (decomp)

EXAMPLE 10

E-4-[2-[6-(2-Phenylethylamino)-hex-3-enylamino]ethyl]-1,2-benzenediol dihydrobromide (a) Methyl E-5-(2-phenylethylaminocarbonyl)pent-3-enoate The sub-title compound was prepared from benzeneethanamine and E-hex-3-enedioic acid monomethyl ester using the procedure of Example 6(a) mp 69°–70°.

(b) E-5-(2-phenylethylaminocarbonyl)pent-3-enoic acid

The product of step (a) (13.9 g., 48 mmoles) and sodium bicarbonate (4.05 g., 48 mmoles) in methanol (300 ml) and water (60 ml) was heated at reflux for 8 hr. The solution was evaporated to dryness and the residue partitioned between water and ethyl acetate. The aqueous phase was separated, acidified with dilute hydrochloric acid, and extracted with ethyl acetate. Evaporation of the organic extracts gave the sub-title compound (9.9 g) mp 101°–103°.

(c) E-N-[2-(3,4-Dimethoxyphenyl)ethyl]-N'-(2-phenylethyl) hex-3-enediamide

The sub-title compound was prepared from the product of step (b) using the procedure of Example 6(b) mp 150°–152°.

(d) E-N-[2-(3,4-Dimethoxyphenyl)ethyl]-N'-(2-phenylethyl)hex-3-ene-1,6-diamine

The product of step (c) (6 g., 14.6 mmoles) and lithium aluminium hydride (1M solution in ether, 60 ml, 60 mmoles) in dry dichloromethane (200 ml) were heated at reflux under nitrogen for 5 hrs. The suspension was cooled and poured slowly into an ice-cold 10% aqueous solution of sodium hydroxide. The organic phase was separated, washed with brine and evaporated. Recrystallisation of the residue from 2-propanol afforded the sub-title compound (2.0 g) mp 270°–272°.

(e) E-4-[2-[6-(2-Phenylethylamino)hex-3-enylamino]ethyl]1,2-benzenediol dihydrobromide The product of step (d) (0.85 g) and cyclohexene (2.35 g) in dry dichloromethane (40 ml) were cooled to -80° and boron tribromide (9.3 ml., of a 1M solution in dichloromethane) was added under nitrogen. The mixture was allowed to warm to room temperature overnight then excess reagent was destroyed by the addition of methanol. The solution was evaporated to dryness and the residue triturated with ethyl acetate to give a grey solid. Recrystalisation from 2-propanol gave the title compound as the dihydrobromide salt (0.3 g) mp 208°–9°.

EXAMPLE 11

4-[2-(9-Phenylnonylamino)ethyl]-1,2-benzenediol (a) N-[2-(3,4-Dimethoxyphenyl)ethyl]-9-phenylnonanamide A solution of 9-phenylnonanoic acid (1.934 g) and N,N'-carbonyldiimidazole (1.34 g) in dry dichloromethane (20 ml) was stirred at 20° for one hour and a solution of 3,4-dimethoxybenzeneethanamine (1.4 ml) in dry dichloromethane (10 ml) then added. The mixture was stirred at 20° for 18 hours and water added. The organic phase was separated, washed with dilute hydrochloric acid, aqueous sodium bicarbonate and brine, dried over magnesium sulphate and evaporated to leave a solid. Crystallisation from 2-propanol gave the amide as colourless prisms (2.7 g); mp, 117°–119°.

(b) N-[2-(3,4-Dimethoxyphenyl)ethyl]-9-phenylnonamine hydrochloride

A solution of the amide from step (a) (2.6 g) in dry tetrahydrofuran (50 ml) was stirred under a nitrogen atmosphere while borane in tetrahydrofuran (13 ml of a 1M solution) was added. The mixture was heated under reflux for 18 hours.

Methanol (50 ml) was added to the cooled solution and the mixture evaporated to dryness. The residue was dissolved in methanolic HCl (50 ml) and heated under reflux for 2.5 hours. The solution was evaporated and the solid crystallised from 2-propanol as colorless prisms (2.4 g); mp, 132°–133°.

(c) 4-[2-[9-Phenylnonylamino]ethyl]-1,2-benzenediol hydrobromide

A solution of the amine from step (b) (1.9 g) in 48% aqueous hydrobromic acid (20 ml) containing hypophosphorous acid (0.1 ml) was heated under reflux in a nitrogen atmosphere for 3 hours. The solution was evaporated to dryness to give the hydrobromide of the title compound, which was crystallised from 2-propanol as colourless flakes (1.3 g); mp, 136.6°–137.7°.

EXAMPLE 12

4-[2-[6-(2-Phenylethylthio)hexylamino)ethyl]-1,2 benzenediol (a) N-[2-[3,4-Bis(phenylmethoxy)phenyl]ethyl]-N-(6-bromohexyl)-2,2,2-trifluorocetamide N-[2-[3,4-Bis(phenylmethoxy)phenyl]ethyl]-2,2,2-trifluoroacetamide (30.6 g, 0.071 mole) in dry dimethylformamide (100 ml) was added dropwise to a suspension of oil free sodium hydride (1.71 g, 0.074 mole) in dry dimethylformamide (100 ml) and the suspension was stirred at 15°–20° for 30 min. 1,6-Dibromohexane (52 g, 0.21 mole) was added and the reaction mixture heated to 60° for 3 hr. The cooled reaction mixture was poured into water and extracted with dichloromethane, the extracts were washed with water, dried (Na2SO4) and evaporated to give an oil which was chromatographed on silica gel eluting with petroleum ether (bp 40°–60° C.): ethyl acetate (10:1) to give the sub-title compound as an oil (35 g), (MS; $m/e$ 591/593).

(b) N-[2-[3,4-Bis(phenylmethoxy)phenyl]ethyl]-N-[6-(2-phenylethylthio)hexyl]-2,2,2-trifluoroacetamide Benzeneethanethiol (5.8 ml) in dry dimethylformamide (50 ml) was added to a suspension of oil free sodium hydride (1.03 g, 0.044 mole) in dry dimethylformamide (150 ml) at 0°. The suspension was stirred for 20 mins and a solution of the product from step (a) (26 g, 0.044 mole) in dry dimethylformamide (150 ml) was added and the mixture stirred at 0° for 1 hour and then allowed to warm to room temperature. The reaction mixture was poured into water and extracted with dichloromethane. The extracts were washed with water, dried (Na2SO4), evaporated and the residue chromatographed on silica gel using petroleum ether (bp 40°–60°): ethyl acetate (20:1) as eluant to give the sub-title compound as an oil (21 g) (MS; $m/e$ 649).

(c)
N-[6-(2-Phenylethylthio)hexyl]-3,4-bisphenylmethoxy) benzeneethanamine

The product from step (b) (7.0 g, 0.011 mole) was heated to reflux for 2 hr with a solution of sodium hydroxide (0.93 g, 0.023 mole) in 90% ethanol (100 ml). The cooled solution was concentrated in vacuo and the residue diluted with water and extracted with dichloromethane. The extracts were washed with water, dried (MgSO$_4$) and evaporated. The residue was dissolved in ether and treated with ethereal-HCl to give the sub-title compound as the hydrochloride salt, a white solid (5.5 g) mp 89°–91°.

(d)
4-[2-[6-(2-Phenylethylthio)hexylamino]ethyl]-1,2-benzenediol

The product from step (c) (0.2 g, 0.03 mmole) was heated to reflux with conc.HCl (2 ml) under nitrogen for 4 hr. The cooled reaction mixture was neutralized with sodium carbonate and extracted with dichloromethane. The combined extracts were evaporated and ethereal-HCl added to give the title compound as the hydrochloride salt (0.05 g) mp 109°–11°.

EXAMPLE 13
4-[2-[6-[2-Phenylethoxy]hexylamino]ethyl-1,2benzenediol (a) 2-[6-Bromohexyloxy]-1-phenylethane A solution of benzeneethanol (12.2 g) in dry dimethylformamide (25 ml) was added dropwise to a stirred suspension of sodium hydride (2.4 g) in dry dimethylformamide (25 ml) under a nitrogen atmosphere. The mixture was heated at 50° for 1 hour and then cooled to room temperature The above mixture was then added dropwise to a stirred solution of 1,6-dibromohexane (36.6 g) in dry dimethylformamide (25 ml) and the solution stirred in a nitrogen atmosphere at 20° for 24 hours The solution was evaporated and the residue quenched with dilute hydrochloric acid and extracted with ethyl acetate. The organic phase was separated washed with brine, dried, filtered and evaporated to leave an oil which was purified by column chromatography (SiO$_2$) eluting with dichloromethane to give a pale yellow oil (11.4 g); MS:m/e 284/286

(b) N-[2-[3,4-Bis(phenylmethoxy)phenyl]ethyl]-2,2,2-trifluoro-N-[6-[2-phenylethoxy]hexyl]acetamide A solution of N-[2-[3,4-Bis(phenylmethoxy) phenyl]ethyl]-2,2,2-trifluoroacetamide (11g) in dry dimethylformamide (30 ml) was added dropwise to a stirred suspension of sodium hydride (0.615 g) in dry dimethylformamide (20 ml) in (a) nitrogen atmosphere. The mixture was heated at 70° C. for 1 hour and then cooled to room temperature.

A solution of the product from step (a) (8.04 g) in dry dimethylformamide (20 ml) was added dropwise and the mixture stirred at 20° under a nitrogen atmosphere for 24 hours.

The solution was evaporated and the residue quenched with dilute hydrochloric acid. The aqueous phase was extracted with ethyl acetate and separated. The organic phase was washed with brine, dried, filtered and evaporated to leave an oil which was purified by column chromatography (SiO$_2$) eluting with 30% ether/60/80 petrol ether to give a colourless oil (8.65); MS m/e 633.

(c)
N-[6-[2-Phenylethoxy]hexyl]-3,4-bis(phenylmethoxy) benzeneethanamine

A solution of the amide from step (b) (8.9 g) in ethanol (50 ml) containing 20% aqueous sodium hydroxide solution (0.63 g) was heated under reflux for 2 hours. The mixture was quenched with water (100 ml) and the solution extracted with chloroform. The organic solution was separated washed with brine, dried, filtered and evaporated to leave a yellow oil.

Trituration with ethereal HCl and crystallisation of the resulting solid from 2-propanol gave the sub-title compound hydrochloride salt as a colourless solid (6.6 g) mp 97.2°–98.6°.

(d)
4-[2-[6-[2-Phenylethoxy]hexylamino]ethyl-1,2-benzenediol

A solution of the product from step (c) (5.7 g) in dry ethanol (200 ml) containing 5% Pd/C (500mg) was hydrogenated at atmospheric pressure for 20 hours.

The solution was filtered and evaporated. The resulting solid was crystallised from cyclohexane to give the title compound hydrochloride salt as colourless solid (1.17 g); mp 116.9°–118°.

EXAMPLE 14
N-6-[2-(3,4-Dihydroxyphenyl)ethylamino]hexyl-N'-phenylurea (a)
Ethyl-6-[N-2-(3,4-bis(phenylmethoxy)phenyl)ethyl-N-phenylmethylamino]hexanoate A suspension of 3,4-bis(phenylmethoxy)-N-phenylmethyl benzeneethanamine (10 g), ethyl 6-bromohexanoate (10.5 g), potassium carbonate (6.34 g) and potassium iodide (1 g) in acetonitrile (250 ml) was heated under reflux for 24 hours.

The suspension was filtered hot and the filtrate evaporated to dryness The residue was dissolved in ethyl acetate and washed with brine, dried over MgSO$_4$, filtered and evaporated to leave a yellow oil which was purified by column chromatography on SiO$_2$ eluting with dichloromethane with 1–3% methanol (12 g). MS m/e 565, base peak 91.

(b)
6-[N-2-(3,4-Bis(phenylmethoxy)phenyl)ethyl-N-ohenyl methylamino]hexanoic acid A solution of the ester from step (a) (10.9 g) and sodium hydroxide (1.7 g) in methanol (400 ml) and water (20 ml) was heated under reflux for 2 hours. The solution was evaporated and the residue acidified with 2N HCl. The aqueous phase was extracted with ethyl acetate. The organic phase was dried over MgSO$_4$, filtered and evaporated to leave a solid which crystallised from ethyl acetate as colourless flakes (7.6 g); mp 124°–126°.

(c)
6-[N-2-(3,4-Bis(phenylmethoxy)phenyl)ethyl-N-phenyl methyl-N-phenylmethylamino]hexanamide A solution of the acid from step (b) (3.5 g) and N,N'-carbonyldiimidazole in dry dichloromethane (20 ml) was stirred at 20° in a nitrogen atmosphere for 2 hours.

0.880 Ammonia (50 ml) was added and the mixture stirred vigorously at 20° for 20 hours.

The mixture was separated and the organic phase washed with brine, dried over MgSO$_4$, filtered and evaporated to leave a solid which crystallised from toluene as colourless flakes (2.7 g), mp 96°–98°.

(d) [N-2-(3,4-Bis(phenylmethoxy)pheny)ethyl-N-phenylmethyl]-1,6-hexanediamine A solution of the amide from step (c) (1.5 g) in dry dichloromethane (20 ml) was cooled to −20° during the dropwise addition of lithium aluminium hydride (6 ml of a 1M solution in ether). The solution was stirred at 20° for 24 hours and heated under reflux for 1 hour.

A 15% solution of sodium hydroxide in water was added to the cooled mixture and the organic phase separated, dried over MgSO$_4$, filtered and evaporated to leave the sub-title compound as a yellow oil (1.1 g); MS m/e 523 (M$^+$+1), base peak 91.

(e) N-[6-(N-(2-(3,4-Bis(phenylmethoxy)phenyl)ethyl)-N-phenylmethyl)aminohexyl]-N'-phenylurea A solution of the amine from step (d) (1.5 g) and phenyl isocyanate (0.31 ml) in dry toluene (20 ml) was stirred at 20° for 18 hours. The solution was evaporated to dryness and the residual oil purified by chromatography on SiO$_2$ eluting with dichloromethane/1% methanol to give the sub-title compound (1.45 g). M.S. m/e 640 (M$^+$−1) base peak 91.

(f) N-[6-(N-(2-(3,4-Dihydroxyphenyl)ethyl)amino]hexyl-N'-phenylurea oxalate

The amine from step (e), as its oxalate salt, (1.3 g) in dry methanol (20 ml) was hydrogenated over a 10% Pd/C catalyst (0.125 g) at atmospheric pressure for three days. The catalyst was removed by filtration and the filtrate evaporated to leave the oxalate salt of the title compound as a solid which crystallised from ethanol (0.3 g); mp 122°–128°.

EXAMPLE 15

N-[6-[2-(3,4-Dihydroxyphenyl)ethylamino]hexyl]benzene acetamide

A solution of triethylamine (2.1 g, 0.021 mole) and the product from Example 14 step (d) (3.0 g, 0.0057 mole) in dichloromethane (50 ml) was stirred and treated dropwise with benzeneacetylchloride (1.2 g, 0.0078 mole). The mixture was stirred at room temperature for 30 min and then heated under reflux for 1 hr. The cooled reaction mixture was poured onto ice and extracted with dichloromethane. The dichloromethane extracts were dried (MgSO$_4$) and evaporated and the residue triturated with ether to give a yellow semi solid. This semi solid was dissolved in dry ethanol (75 ml) and hydrogenated at room temperature and atmospheric pressure with 10% palladium on charcoal (0.2 g). The catalyst was removed by filtration and the filtrate evaporated and triturated with ether. The solid obtained was partitioned between chloroform and aqueous sodium bicarbonate solution and the chloroform extracts washed with water, dried (MgSO$_4$) and evaporated. The residue was dissolved in ethanol (15 ml), a solution of oxalic acid (0.8 g) in ethanol (10 ml) added. The resulting solution concentrated to half its original volume and diluted with ether. The resulting solid was isolated washed with ether-ethanol, dried at 70° in vacuo to give the title compound as the oxalate salt (0.35 g) mp 122°–126°.

EXAMPLE 16

4-[2-[6-(2,3-Dihydro-1H-inden-2-ylamino)hexylamino]ethyl]-1,2-benzenediol

(a) N-(2,3-Dihydro-1H-inden-2-yl)-N'-[2-(3,4-dimethoxyphenyl)ethyl]hexanediamide 6-[2-(3,4-Dimethoxyphenyl)ethylamino]-6-oxohexanoic acid (6.0 g, 0.019 mole) was dissolved in dry dichloromethane (200 ml) and triethylamine (2.28 g, 0.021 mole) added followed by ethyl chloroformate (1.86 ml, 0.019 mole) at 0°. The solution was stirred at 0° for 30 min and a solution of 2-aminoindane hydrochloride (3.3 g, 0.019 mole) and triethylamine (2.52 ml 0.019) in dry dichloromethane (200 ml) added, allowed to warm to room temperature and stirred for a further 18 hr. The reaction mixture was washed with water, dried (MgSO$_4$) and evaporated and the residue recrystallised from methanol to give the sub-title compound as a white solid (6.4 g), mp 162°–4°.

The following intermediates were prepared by the process of step (a)
(i) N-[2-(3,4-Dimethoxyphenyl)ethyl]-N'-[2-(2- methyl-2-phenyl)propyl]hexanediamide mp 121°–4°
(ii) N-[2-(3,4-Dimethoxyphenyl)ethyl]-N'-(1,1- dimethyl-2-phenyl ethyl)hexanediamide MS m/e 440, base peak 164.

(b) N-(2,3-Dihydro-1H-inden-2-yl)-N'-[2-(3,4-dimethoxyphenyl)ethyl]-1,6-hexanediamine A mixture of the product from step (a) (2.0 g, 4.7 mmole) sodium borohydride (0.71 g, 18.9 mmole), boron trifluoride etherate (3.41 g, 24.5 mmole) in dry tetrahydrofuran (100 ml) was heated to reflux for 14 hr. Methanol was added to the cooled reaction mixture to destroy the excess diborane and the mixture concentrated in vacuo. The residue was diluted with water and extracted with dichloromethane. The combined extracts were dried (Na$_2$SO$_4$) and evaporated. The residue was heated to reflux with methanolic-HCl (30 ml) for 1 hr, further methanol being added to dissolve the precipitated solid. The cooled reaction mixture afforded the sub-title compound as the dihydrochloride salt (1.6 g) mp 270° dec.

The following intermediates were prepared by the process of step (b):
(i) N-[2-(3,4-Dimethoxyphenyl)ethyl]-N'-[2-(2-methyl-[2-phenyl) propyl]-1,6-hexanediamine dihydrochloride mp 197°–9°.
(ii) N-[2-(3,4-Dimethoxyphenyl)ethyl]-N'-(1,1-dimethyl-2-phenyl ethyl)-1,6-hexanediamine dihydrochloride mp 240°–3°.

(c) 4-[2-[6-(2,3-Dihydro-1H-inden-2-ylamino)hexylamino]ethyl]-1,2-benzenediol The product from step (b) (1.25 g, 2.67 mmole) was suspended in 48% aqueous hydrobromic acid (35 ml) and hypophosphorous acid (0.3ml) and the mixture heated to reflux for 3.5 hr. The excess acid was removed in vacuo and the residue recrystallised from methanol to give the title compound as the dihydrobromide salt (1.15 g), mp 215°-7°.

EXAMPLE 17

The following compounds were made from the process of Example 16(c) from the corresponding intermediates described in Example 16.
(i) 4-[2-[6-(2-Methyl-2-phenylpropylamino)hexylamino]ethyl]1,2-benzenediol dihydrobromide mp 169°-72°,
(ii) 4-[2-[6-(1,1-dimethyl-2-phenyl- ethylamino)hexylamino]ethyl]-1,2-benzenediol dihydrobromide mp 224°-6°.

EXAMPLE 18

4-[2-(6-[2-(Phenylamino)ethylamino]hexylamino]ethyl]1,2-benzenediol (a)
N-[2-(3,4-Dimethoxyphenyl)ethyl]-N'-[2-(phenylamino) ethyl]hexanediamide 6-[2-(3,4-Dimethoxyphenyl)ethylamino]-6-oxohexanoic acid (6.0 g, 0.19) was dissolved in dry dichloromethane (200 ml) and triethylamine (2.28 g, 0.021 mole), and ethyl chloroformate (1.86 ml, 0.019 mole) added at 0°. After 1 hour at 0° N-phenyl-1,2-ethanediamine (2.64 g, 0.019 mole) was added and the mixture stirred at room temperature for 18 hr. After washing with water and drying (Na$_2$SO$_4$), the reaction mixture was evaporated and the residue recrystallised from ethyl acetate to give the sub title compound (5.3 g) mp 109°-11°.

The following intermediates were prepared by the process of step (a):
(i) N-[2-[3,4-Bis(phenylmethoxy)phenylethyl]-N'[2-phenoxyethyl]hexanediamide, mp 133-6°;
(ii) N-[2-[3,4-Bis(phenylmethoxy)phenyl]etheyl]-N-[2-phenylthioethyl]hexanediamide, mp 131°-3°.

(b)
N-[2-(3,4-dimethoxyphenyl)ethyl]-N'-[2-(phenylamino) ethyl]-1,6-hexanediamine A mixture of the product from step (b) (5.0 g, 0.012 mole) sodium borohydride (1.8 g, 0.47 mole) and boron trifluoride etherate (8.6 g, 0.061 mole) in dry tetrahydrofuran (250 ml) was heated to reflux for 18 hr. Methanol was added to the cooled reaction mixture to destroy the excess diborane and the mixture was concentrated in vacuo. The residue was diluted with water and extracted with dichloromethane. The combined extracts were washed with water, dried (Na$_2$SO$_4$) and evaporated. The residue was dissolved in methanolic-HCl (100 ml) and heated to reflux for 2 hrs and after concentration of the reaction mixture to about half the original volume the sub-title compound was obtained as the trihydrochloride salt on cooling as a white solid (2.5 g) mp 190° (dec).

The following intermediates were prepared by the process of step (b);
(i) N-[2-[3,4-Bis(phenylmethoxy)phenyl]ethyl]-N'-(2-phenoxyethyl)-1,6-hexanediamine dihydrochloride, mp 230°-3°;
(ii) N'-[2-[3,4-Bis(phenylmethoxy)phenyl]ethyl]-N-[-2(Phenylthio)ethyl]-1,6-hexanediamine dihydrochloride, mp 167°-7°.

(c)
4-[2-[6-[2-(Phenylamino)ethylamino]hexylamino]ethyl]-1,2-benzenediol

A mixture of the product from step (b) (2.0 g, 3.9 mmole), 48% aqueous hydrobromic acid (50 ml) and hypophosphorous acid (0.2 ml) was heated to reflux for 4 hrs. After cooling the precipitated solid was recrystalised from methanol to give the title product as the trihydrobromide salt (2.1 g) mp 177°-9°.

EXAMPLE 19

4-[2-[6-(2-Phenyloxyethylamino)hexylamino]ethyl]-1,2-benzenediol

A mixture of the intermediate (i) from Example 18(b) (0.3 g, 0.62 mmole) concentrated hydrochloric acid (20 ml) and hypophosphorous acid (0.2 ml) was heated to reflux for 5 hr. After cooling the precipitated solid was isolated, washed with ether and direct to give the title product as the dihydrochloride salt (0.13 g), mp 158°-61°.

EXAMPLE 20

4-[2-[6-[2-(Phenylthio)ethylamino]hexylamino]ethyl]-1,2benzenediol

A mixture of the intermediate (ii) from Example 18(b) (1.0 g, 1.76 mmole), concentrated hydrochloric acid (25 ml) and hypophosphorous acid (0.3 ml) was heated to reflux for 6 hours under an atmosphere of nitrogen The solution was evaporated to dryness, dissolved in water, neutralized with sodium carbonate and the mixture extracted with dichloromethane. The combined extracts were washed with water, dried (MgSO$_4$) and evaporated. The residue was dissolved in the minimum of methanol and a saturated solution of oxalic acid in methanol added. The precipitated solid was isolated and dried to give the title product as the oxalate salt (0.2 g) mp 166°-8°.

EXAMPLE 21

6-[2-(3,4-Dihydroxyphenyl)ethylamino]-N-(2-phenylethyl) hexanamide (a)
6-[N-[2-[3,4-Bis(phenylmethoxy)phenyl]ethyl]-N-phenyl methylamino]-N-(2-phenylethyl)hexanamide 6-[N-[2-[3,4-Bis(phenylmethoxy)phenyl]ethyl]-N-phenyl methylamino]hexanoic acid (5.37 g, 0.01 mole) and triethylamine (1.53 ml, 0.012 mole) were dissolved in dry dichloromethane (50 ml) and the solution cooled to 0°. To this solution was added a solution of ethyl chloroformate (0.95 ml, 0.01 mole) in dry dichloromethane (10 ml). The mixture was stirred at 0° for 30 min and a solution of benzeneethanamine (1.25 ml, 0.01 mole) in dry dichloromethane (10 ml) added and stirring continued for 2 hr at 0°. The reaction mixture was warmed to room temperature, washed with 2N HCl and water, dried (Na$_2$SO$_4$) and evaporated. The residue was triturated with boiling petroleum ether (bp 40-60°) to give the sub title compound (3.5 g) mp 66°-8°.

(b)
6-[2-(3,4Dihydroxyphenyl)ethylamino]-N-(2-Phenylethyl) hexanamide

The product from step (a) (2.7 g, 4.2 mmole) was dissolved in ethanol (250 ml) and hydrogenated at room temperature and at atmospheric pressure in the presence of 5% palladium on charcoal (0.5 g) for 3 hr. The catalyst was removed by filtration and the filtrate evaporated. The residue was dissolved in the minimum of methanol and a saturated solution of oxalic acid in methanol added. The solid product was isolated and digested with boiling methanol to give the title compound as the hemi-oxalate containing half a mole of methanol of crystallisation.(0.5 g). mp 191°-2°.

EXAMPLE 22

2-Phenylethyl 6-[2-(3,4-dihydroxyphenyl)ethylamino]hexanoate

6-[N-[2-[3,4-Bis(phenylmethoxy)phenyl]ethyl]-N-phenylmethylamino]hexanoic acid (5.37 g, 0.01 mole) and triethylamine (1.52 ml, 0.012 mole) were dissolved in dry dichloromethane (50 ml) and the solution cooled to 0°. To this solution was added ethylchloroformate (0.96 ml, 0.01 mole). The mixture was stirred at 0° for 30 mins and a solution of benzeneethanol (1.25 ml, 0.01 mole) added and stirring continued at 0° for 2 hrs. The reaction mixture was warmed to room temperature and washed with water, dried ($Na_2SO_4$) and evaporated to give an oil that was chromatographed on silica gel using petroleum ether (bp 40°-60°)-methanol (100:2) as eluant. The 0,0,N tribenzyl ester was isolated as an oil (3.0 g).

This oil was dissolved in ethanol (100 ml) and hydrogenated at room temperature and 5 atmospheres pressure in the presence of 5% palladium on charcoal (0.5 g) for 4 hrs. The catalyst was removed by filtration and the filtrate evaporated. The residue was taken up in the minimum of methanol and treated with a saturated solution of oxalic acid in methanol The title compound was isolated from the cooled solution as the mono oxalate salt (0.2 g) mp 131°-2°.

What we claim is:

1. A compound of formula I,

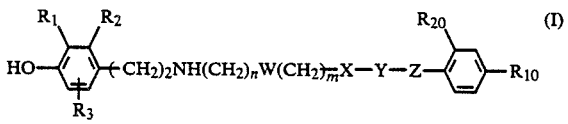

in which $R_1$ represents OH, $R_2$ and $R_3$, which may be the same or different, each independently represent hydrogen, fluorine, chlorine, bromine, alkyl C1 to 6, nitro, $(CH_2)_p R_9$ or $SR_9$, W represents a single bond, a 1,2-,1,3-, or 1,4-phenylene ring; a —CH=CH—group or a 1,4-cyclohexanediyl group;

Z represents a single bond, $NR_{19}$, or $CH_2$, in which $R_{19}$ represents hydrogen or alkyl C1 to 6;

n and m each independently represent an integer from 1 to 4 inclusive;

p represents 0 or an integer from 1 to 3 inclusive;

$R_9$ represents phenyl or phenyl substituted by hydroxy, $R_{10}$ represents hydrogen or chlorine, and X represents NH, Y represents CO, and $R_{20}$ represents hydrogen or X represents CONH, Y represents $(CH_2)_q$, wherein q represents an integer from 1 to 3 inclusive, and $R_{20}$ represents hydrogen, and pharmaceutically acceptable derivatives thereof.

2. A compound according to claim 1 wherein W represents a single bond.

3. A compound according to claim 1 wherein Y represents $(CH_2)_q$.

4. A compound according to claim 1 wherein Z represents a single bond.

5. A compound according to claim 1 wherein X represents NH and Y represents CO.

6. A compound according to claim 1 wherein X represents CONH and Y represents $(CH_2)_q$.

7. A compound in accordance with claim 1, which is selected from the group consisting of
N-[6-[2-(3,4-dihydroxyphenyl)ethylamino]hexyl]benzene acetamide
6-[2-(3,4-dihydroxyphenyl)ethylamino]-N-(2-phenylethyl)hexanamide,
and pharmaceutically acceptable salts thereof.

8. A pharmaceutical composition comprising a compound according to claim 1 in admixture with a pharmaceutically acceptable adjuvant, diluent or carrier.

9. A method of treatment of a cardiac disorder, which method comprises administration to a patient suffering from such a condition of a therapeutically useful amount of a compound in accordance with claim 1.

* * * * *